United States Patent
Ostrum et al.

(10) Patent No.: US 9,649,338 B2
(45) Date of Patent: May 16, 2017

(54) USE OF SILVER-CONTAINING LAYERS AT IMPLANT SURFACES

(71) Applicants: Robert Ostrum, Glassboro, NJ (US); Jeffrey Hettinger, Glassboro, NJ (US); Robert Krchnavek, Glassboro, NJ (US); Gregory A Caputo, Glassboro, NJ (US)

(72) Inventors: Robert Ostrum, Glassboro, NJ (US); Jeffrey Hettinger, Glassboro, NJ (US); Robert Krchnavek, Glassboro, NJ (US); Gregory A Caputo, Glassboro, NJ (US)

(73) Assignee: Rowan University, Glassboro, NJ (US)

(*) Notice: Subject to any disclaimer, the term of this patent is extended or adjusted under 35 U.S.C. 154(b) by 0 days.

(21) Appl. No.: 13/784,653

(22) Filed: Mar. 4, 2013

(65) Prior Publication Data
US 2013/0344123 A1    Dec. 26, 2013

Related U.S. Application Data

(60) Provisional application No. 61/605,946, filed on Mar. 2, 2012.

(51) Int. Cl.
*A61K 33/38*       (2006.01)
*A61L 15/46*       (2006.01)
(Continued)

(52) U.S. Cl.
CPC .............. *A61K 33/38* (2013.01); *A61L 15/46* (2013.01); *A61L 27/54* (2013.01); *A61L 29/103* (2013.01);
(Continued)

(58) Field of Classification Search
CPC .......... A61K 33/38; A61L 15/46; A61L 31/16; A61L 29/103; A61L 29/16; A61L 27/54;
(Continued)

(56) References Cited

U.S. PATENT DOCUMENTS 5,180,585 A * 1/1993 Jacobson et al. ............. 424/405
5,454,886 A * 10/1995 Burrell ................... A01N 59/16
                                                    148/565
(Continued)

OTHER PUBLICATIONS

KD et al. "Nanoparticle silver ion coatings inhibit biofilm formation on titanium implants", J. Clin. Neurosci. 18(3):391-3955, E-published on Jan. 20, 2011 (abstract).*
(Continued)

*Primary Examiner* — Ernst V Arnold
*Assistant Examiner* — Kyung Sook Chang
(74) *Attorney, Agent, or Firm* — Fox Rothschild LLP; Shahnam Sharareh; Robert N. Henrie, II

(57) ABSTRACT

The disclosure relates to coatings that contain silver, either in the form of metallic silver, silver oxides, salts of silver, or combinations of these. The silver is present in a microparticulate or nanoparticulate form, which exerts antimicrobial activity when bacteria (e.g., in a body fluid) contact the coated surface. The coatings are applied through accumulation of silver-containing particles on the surface, such as by sputtering or electron beam vapor deposition. As a result, their thickness, particle size, and density can be controlled. Furthermore, the surface can also be coated with other substances, such as diamond-like carbon or alumina, either as a discrete layer or intermixed with the silver-containing particles.

19 Claims, 4 Drawing Sheets

(51) Int. Cl.
　　　A61L 31/16　　　(2006.01)
　　　A61L 29/10　　　(2006.01)
　　　A61L 29/16　　　(2006.01)
　　　A61L 27/54　　　(2006.01)
　　　A61K 31/08　　　(2006.01)
　　　A61L 31/08　　　(2006.01)
(52) U.S. Cl.
　　　CPC ............. *A61L 29/16* (2013.01); *A61L 31/084* (2013.01); *A61L 31/16* (2013.01); *A61L 2300/104* (2013.01); *A61L 2300/404* (2013.01); *A61L 2300/622* (2013.01)
(58) Field of Classification Search
　　　CPC ............. A61L 31/084; A61L 2300/404; A61L 2300/622; A61L 2300/104
　　　See application file for complete search history.

(56) References Cited

U.S. PATENT DOCUMENTS 5,476,881 A * 12/1995 Suh ............................... 523/122
6,361,567 B1 * 3/2002 Dearnaley .................. 623/23.73
2007/0203574 A1 * 8/2007 McGrath et al. ............ 623/1.46
2009/0247973 A1 * 10/2009 Yeh et al. ..................... 604/360
2010/0074934 A1 * 3/2010 Hunter .......................... 424/422
2011/0014258 A1 * 1/2011 Gan et al. ..................... 424/409

OTHER PUBLICATIONS

KD et al. "Nanoparticle silver ion coatings inhibit biofilm formation on titanium implants", J. Clin. Neurosci. 18(3):391-395, E-published in 2011 (full text).*

Lu et al., "Nano-Ag-loaded hydroxyapatite coatings on titanium surfaces by electrochemical deposition", Journal of the Royal Society Interface (2011) 8, pp. 529-539, on-line published on Sep. 29, 2010 ([retrieved by on-line download from website: rsif.royalsocietypublishing.org, on Jun. 6, 2014]).*

Wikipedia "Sapphire", [retrieved by on-line download from website: http://en.wikipedia.org/wiki/Sapphire, on Jun. 12, 2014].*

Kent, Ronald D. et al., Controlled Evaluation of Silver Nanoparticle Dissolution Using Atomic Force Microscopy, American Chemical Society, Environ. Sci. Technol. 2012, 46, 6977-6984.

* cited by examiner

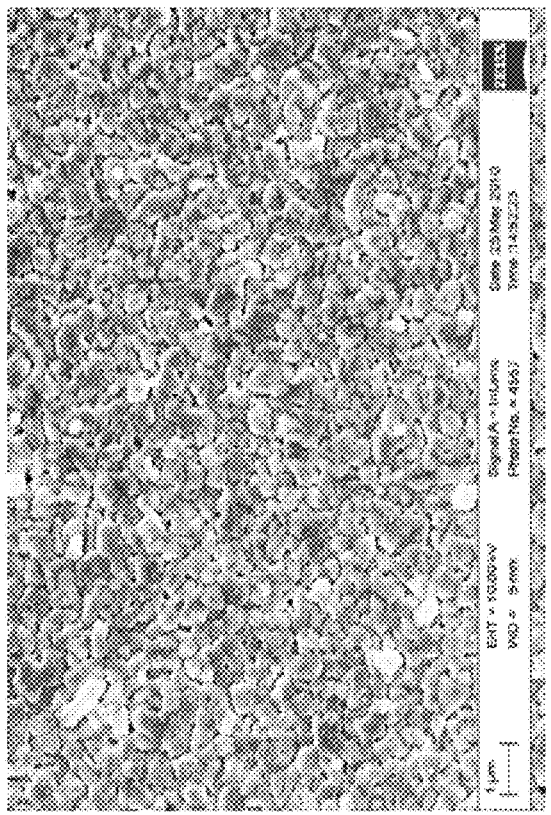 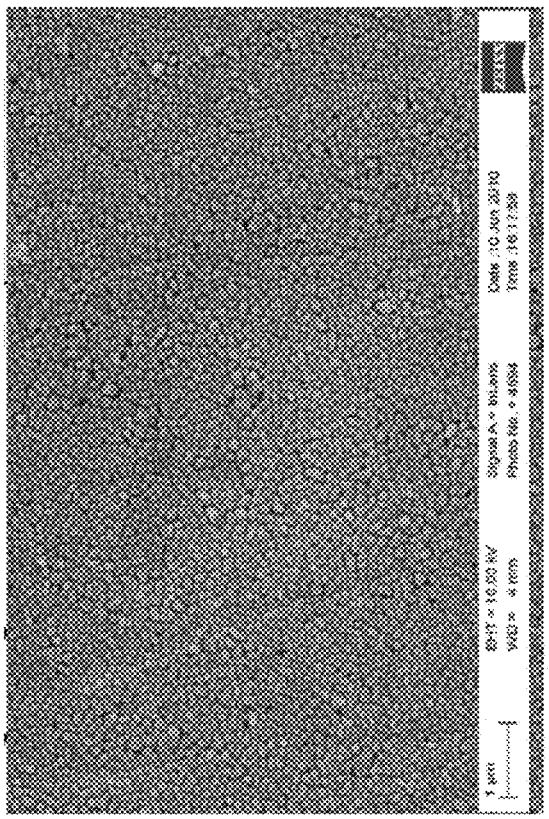
Fig. 1A
Fig. 1B

USE OF SILVER-CONTAINING LAYERS AT IMPLANT SURFACES

CROSS-REFERENCES TO RELATED APPLICATIONS

This application is entitled to priority pursuant to 35 U.S.C. §119(e) to U.S. provisional patent application 61/605,946, which was filed on 2 Mar. 2012.

BACKGROUND OF THE DISCLOSURE

The disclosure relates generally to the field of coatings for articles intended for permanent or temporary implantation into animals such as humans.

Infection is a serious complication of devices implanted in the human body (Klevens et al., 2007, J. Am. Med. Assoc. 298:1763). Deep infections, which are difficult to treat may often require removal of the infected implant to eradicate infection and this remains a serious complication of major orthopedic medical procedures utilizing endoprostheses (Rabih et al., 2004, N. Eng. J. Med. 350:1422; Fitzgerald, 1995, J. Am. Acad. Ortho. Surg. 3:249; Khan et al., 2008, J. Ayub. Med. Coll. Abbottabad 20:23). Treatment of deep infections is challenging because it is difficult to supply antibiotics to the infection site, and such treatment can vary from 3 to 14 months in duration (Darouiche, 2004, N. Eng. J. Med. 350:1422) and can include secondary surgery (Furno et al., 2004, J. Antimicrob. Chemother. 54:1019).

The most well-known medical procedures involving orthopedic implants are knee and hip replacement surgeries, with an estimated 940,000 such procedures performed in the U.S. in 2005 (Merrill et al., 2007, Statistical Brief 34, Healthcare Cost and Utilization Project). Other known joint replacement procedures include those of the shoulder, elbow, finger, and ankle.

Titanium implants are used to stabilize fused vertebrae (Foley et al., 2002, Clin. Neurosurg. 49:499; Foley et al., 2003, Spine 28:S26). Another orthopedic use of titanium in the body is to provide alignment for a healing bone with either internal or partially external fixation devices (Rantanen et al., 1998, J. Orthop. Trauma 12:249). Although infection is high in hip (~0.75%) and knee (1.5%) replacements, it is even higher in trauma cases (greater than 10%) with open wounds (Ridgeway et al., 2005, J. Bone Joint Surg. Br. 87:844; Wilson et al., 2008, Infect. Control Hosp. Epidemiol. 29:219; Agency for Healthcare Research and Quality, 2003, "Total Knee Replacement Summary—Evidence Report/Technology Assessment", US Department of Health and Human Services; Miclau et al., 2010, J. Orthop. Trauma. 24:583).

Infection rates have increased substantially in recent years. Between the years of 1999 and 2005, infection contracted during hospital visits increased by 62% while the number of hospital visits increased by only 8% (Klein et al., 2007, Emerg. Inf. Dis. 13:1840). Although antibiotics and procedures improved over this time period, infection rates nonetheless increased at an accelerated rate. This can be explained by rapidly increasing development of drug-resistant bacterial strains (Miclau et al., 2010, J. Orthop. Trauma. 24:583).

Development of antibiotic resistance has been recognized as a significant threat to public health and, as a result, is among the highest priorities of several expert committees such as the Institute of Medicine, the American Society for Microbiology, and the U.S. Office of Technology Assessment (Forum on Emerging Infections, 1998, "Antimicrobial Resistance: Issues and Options," Institute of Medicine, Washington D.C.; American Society of Microbiology, 1997, "New and Reemerging Infectious Diseases: A Global Crisis and Immediate Threat to the Nation's Health, The Role of Research," Washington D.C.; Office of Technology Assessment, 1994, "Impacts of Antibiotic Resistant Bacteria," Report OTA-H-629, U.S. Congress, Washington, D.C.; Report of the ASM Task Force on Antibiotic Resistance, 1994, American Society of Microbiology, Washington D.C.). Clearly, antibiotic use must be limited and alternative treatments must be sought.

Due to the large number of patients and the significant percentage of that group who develop infection, almost any contribution in this area can be important for improving both patient recovery and the financial cost of implantation procedures. When a patient gets an infection, the stay in the hospital is extended by six days on average. This represents a significant increase in cost of treatment impacting health care related costs for everyone. The monetary impact of infection alone is exceeding $40 billion annually (Douglas et al., 2009, "The Direct Medical Costs of Healthcare-Associated Infections in U.S. Hospitals and the Benefits of Prevention", Report of the U.S. Centers for Disease Control and Prevention).

Others have previously recognized the antimicrobial properties of silver (Ag), especially in a micro- or nanoparticulate form, and there is extensive literature reporting that effect. Those observations have motivated others to attempt to incorporate Ag into and onto implantable medical devices. Others have described bactericidal coatings containing Ag nanoparticles in polymers, for example. Ag nanoparticles exhibit higher solubility of Ag and Ag ions than continuous Ag films due to their large surface to volume ratio. However, such polymer carriers can be detrimental to the patient.

A common shortcoming of known Ag-containing coatings is that efforts to improve adherence of such coatings (e.g., to provide durability and scratch-resistance) can adversely affect their antimicrobial properties. Conversely, efforts to improve the antimicrobial efficacy of Ag-containing coatings can adversely affect their ability to stably adhere to implant surfaces.

The subject matter disclosed herein overcomes at least some of these shortcomings by providing Ag-containing coatings (and methods of making them) that exhibit both favorable antimicrobial properties and favorable (i.e., stable and durable) physical properties.

BRIEF SUMMARY OF THE DISCLOSURE

This disclosure relates to articles that are implantable in an animal, the article including a microparticulate Ag-containing antimicrobial layer stably adhered upon at least one surface of the article (e.g., upon one face or upon substantially the entire surface of the article). In one embodiment, the antimicrobial layer is composed substantially entirely of microparticulate Ag metal. The layer can include multiple types of microparticulates, such as one or more of Ag, AgO, $Ag_2O$, $AgO_{1-x}N_x$, and $Ag_2O_{1-x}N_x$. The size of the Ag-containing particles is preferably not greater than about 2 micrometers, and is preferably in the ranges 10-2000, 100-1500, or 200-750 nanometers.

The antimicrobial layer can include or be coated with other materials, such as alumina or diamond-like carbon (DLC). By way of example, these materials can be uniformly mixed, laminated as separate layers (e.g., a porous layer enclosing the antimicrobial layer), or mixed such that the composition varies in different portions of the layer.

The disclosure also relates to methods of inhibiting bacterial infection associated with the implantation of an article in an animal. This method includes the step of stably adhering a microparticulate silver-containing antimicrobial layer upon at least one surface of the article prior to implanting the article in the animal. The antimicrobial layer can be adhered, for example, by sputtering silver-containing microparticles onto the surface or by electron beam vapor deposition of silver-containing microparticles onto the surface.

BRIEF SUMMARY OF THE SEVERAL VIEWS OF THE DRAWINGS

FIG. 1 consists of FIGS. 1A and 1B and is a pair of scanning electron micrographs (SEMs) of silver films deposited on polished titanium substrates using methods described herein. The thicknesses of the films shown in the two figures are similar yet the microstructure varies significantly with the individual Ag crystallites in FIG. 1A being almost an order-of-magnitude larger than the crystallites in FIG. 1B. These differences are a result of the deposition parameters.

FIG. 2 consists of FIGS. 2A, 2B, and 2C, and is a trio of graphs of preliminary data on the silver grain size obtained in experiments described herein.

DETAILED DESCRIPTION

Figure 2A:
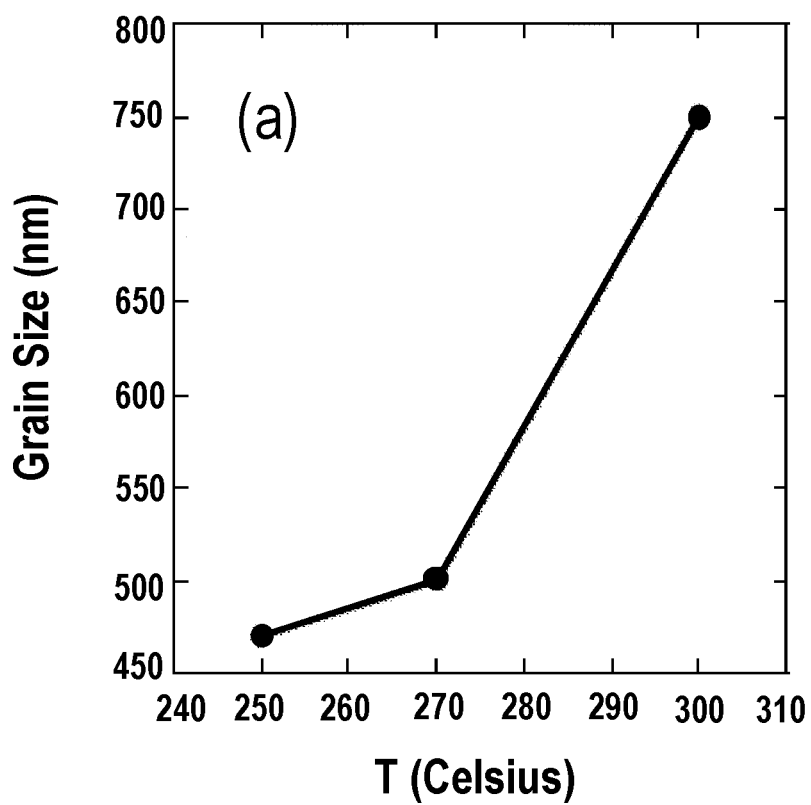
In FIG. 2A, grain size is reported as a function of the temperature used during deposition.

The disclosure relates to implantable articles having surfaces which inhibit, prevent, or reduce bacterial infection associated with the implant.

Infection can occur in many situations which includes many medical procedures. In this disclosure, we focus on controlling infections associated with orthopedic implants. Nonetheless, most or all of what is disclosed is applicable to any implanted medical device, whether it is implanted only temporarily (e.g., surgical instruments, catheters, or drug depots) or more nearly permanently (e.g., vascular stents, prosthetic joints, or pacemaker components).

Significantly reducing the infection rate in orthopedic procedures is an important outcome of the subject matter described herein. However, the multi-functional coatings described herein strongly adhere to implants and their physical and antimicrobial properties can be modified in conventional ways to make them fit for many specific applications. Among the functions envisioned for the coatings described herein are antimicrobial, bio-compatible, bio-inert, friction-reducing, hardness-increasing, and bone-growth inducing functions. Coatings can, of course, achieve more than one of those functions.

Deposition of Ag on metals typically requires a deposition temperature of at least 300° C. in order to achieve strong adhesion. That temperature requirement can significantly impact production costs since the time required to heat and cool the coated object can be on the order of hours since coating occurs in a vacuum. Furthermore, many materials (e.g., many plastics) simply cannot tolerate such high temperatures. Co-deposition of Ag with carbon or various glasses allows strong adhesion at lower temperatures, such as at room temperature (25° C.). The compositions and methods described herein exhibit improved adherence of Ag to implant surfaces, relative to many previously known implants.

Ag is not a particularly hard metal. However by mixing Ag with various glasses, the hardness and durability of a Ag-containing coating can be improved. For example, mixing Ag and diamond-like carbon (DLC) as described herein can dramatically improve the hardness over metallic Ag. Because some implants, such as intramedullary nails are "forced" into position, increasing hardness of the coating can decrease damage to the coating and the concomitant loss of function. The improved hardness of coating described herein, relative to previously known coatings, can be beneficial.

Glasses and other materials (e.g., DLC) are relatively bio-inert and coating an implant with such materials results in "hiding" the implant from the biological system of the animal into which it is implanted. This can suppress the formation of biofilms which can cause implant complications. This can also suppress reduction of the bactericidal effectiveness of the Ag contained in the implant or its coating, because a biofilm can limit Ag release from the implant. Suppression of bioadhesion (and consequent biofilm formation) can improve biocompatibility of implants described herein and enhance the antimicrobial effectiveness of the coatings described herein.

Some brittle coatings (e.g., DLC) cannot be deposited directly onto flexible substrates, such as many polymers. However, it is possible to deposit such coatings onto flexible substrates if the substrate is first coated with a flexible layer of a glass, such as a borosilicate glass. Described herein are coatings which combine Ag, a glass, and a DLC to form hard Ag-containing coatings suitable for application to polymer implants. The compositions and methods described herein thus increase the range of substrates to which Ag, DLC, and their combinations can be applied.

The information disclosed herein indicates that Ag can be mixed with glass or carbon (e.g., DLC) substrates to create uniform heterostructured coatings that modulate dissolution of Ag into the biological system. Such materials facilitate tailoring of bactericidal properties and the effective lifetime of the coatings to desired values.

Details of the components of the coated implants and the methods of making them are now disclosed.

Coated Implants

The coating compositions and methods described herein can be used to coat some or all surfaces of an implant, such as one or more surfaces that are anticipated to contact a tissue or body fluid of an animal for which the implant is intended. Examples of such implants include intramedullary nails, orthopedic implant components (e.g., pins, rods, plates, and screws), artificial joints, artificial heart components (e.g., valves or vessels), synthetic blood vessels such as synthetic arteries, catheters, stents, pacemaker components (e.g., the outer case), nerve-interface electrodes, surgical tools (e.g., scalpels, scissors, and retractors), surgical tables, wound dressings, surgical stitching fibers and meshes, and pharmaceutical packaging such as depots containing a pharmaceutically active agent.

For some orthopedic implants (e.g., portions of knee and hip replacement prostheses), adhesion of bone to the implant is desirable. In other cases, such as intramedullary implants, bone adhesion is detrimental since it makes it very difficult to remove the implant. Sputter deposition allows localized application of surface coatings and has been shown to be a useful technique for applying calcium phosphate [$Ca_5(PO_4)_3(OH)$] which is also called hydroxyapatite (HA) (Yang et al., 2005, Biomaterials 26:327; Boyd et al., 2008, Mater. Sci. Eng. 28:228; Feddes et al., 2003, J. Appl. Phys. 93:662; O'Kane et al., 2008, Surface & Coatings Technol. 203:121). Thin-film coatings of HA have been shown to stimulate rapid bone ingrowth on titanium substrates (Seydlova et al., 2006, J. Appl. Phys. 99:014905; Li et al., 2008, Biomaterials 29:2025). Tests have been performed on as-grown HA films as well as those undergoing a post-deposition anneal and both demonstrated accelerated bone growth. HA films can be used in the coatings described herein, and the coatings can be applied to the exterior of a thin HA film, intermixed therewith, or a combination of these.

Thin-films, such as the Ag-containing films described herein, can be readily synthesized using sputtering techniques, which are known in the art. Such techniques can be used to create films of various thicknesses, ranging from the thickness of a single sputtered microparticle to thick films formed by accumulation of such particles, such as films on the order of 10 or 100 nanometers, or up to 1-10 micrometers or more in thickness. Sputtered films have several major advantages when compared to films grown using other technologies. One advantage is that sputtered films exhibit excellent adhesion to many substrate materials. Another is that sputtering facilitates compositional control when deposition from multiple sources is performed. For instance, use of multiple sources facilitates deposition of discrete layers of different materials, mixing of sputtered materials at the atomic level, or a combination of these. When the sputtered material is reactive with a gas present in the sputtering workspace, reaction of the material and the reactive gas permits deposition of the resulting reaction product. Sputtering techniques are also suitable for deposition for a broad range of materials.

Others have reported the antimicrobial effects of metals and metal oxides, including Ag and Ag oxides (Huang et al., 2005, J. Inorg. Biochem. 99:986; Sawai et al., 2000, World J. Microbiol. Biotechnol. 16:187; Top et al., 2004, Appl. Clay Sci. 27:13; Yamamoto et al., 2000, Int. J. Inorg. Mater. 2:451). In addition to Ag, other metals are known to exhibit antimicrobial effects and can be used in place of Ag in this disclosure. Those metals include Au, Pt, Pd, Ir, Sn, Cu, Sb, Bi, and Zn (each represented by its standard two-letter elemental abbreviation). The antimicrobial property of metals is exhibited even when metals are mixed with other materials (Onodera et al., 2001, Appl. Clay Sci. 18:123).

Generally, metals are simple to convert from a bulk material into a thin-film form, making them attractive to work with and relatively inexpensive to apply on a large scale. Some metals, specifically Ag, have been shown to be effective as a broad-spectrum bactericide even against drug-resistant strains (Lara et al., 2009, World J. Microbiol. Biotechnol. 26:215). Given that most forms of Ag demonstrate some bactericidal properties, Ag is preferred as the metal for the coating described herein.

Improvement of the mechanical properties of orthopedic implants can be achieved with the application of hard coatings, such as coating layers of diamond-like-carbon (DLC). DLC is known in the art, as are methods of making it. DLC is an amorphous carbon film in which a substantial percentage of inter-carbon interactions take the form of diamond-like-bonds. On account of its structure, DLC coatings can achieve as much as approximately 80% of the hardness of diamond. Others have demonstrated biological compatibility of DLC materials with biological systems (Chowdhury et al., 2004, J. Mater. Proc. Technol. 153-154: 804; Michel et al., 2006, Thin Solid Films 496:481). DLC coatings reduce surface friction for loaded mechanical applications and are considered bio-inert materials (Thompson et al., 1991, Biomaterials 12:37; Dearnaley et al., 2005. Surface & Coatings Technol. 200:2518).

DLC can be used as a permeation barrier which can be used to adjust the rate at which Ag ions dissolve into biological fluids (Ozeki et al., 2009, Appl. Surface Sci. 255:7286). DLC materials can be applied to almost any substrate material, although a thin layer of a glass such as sputtered borosilicate may be necessary to achieve adhesion (Maharizi et al., 1999, J. Optoelectron. Adv. Mater. 1:65).

The implants described have a coating which includes Ag. In one embodiment, Ag is intermixed with a DLC material, and the mixed material is laid down (e.g., via simultaneous sputtering from discrete Ag and DLC sputtering cathodes) as a substantially homogenous DLC-Ag matrix. HA can also be co-sputtered with Ag, or with both Ag and DLC to form similarly substantially homogenous matrices. Alternatively, or in addition, discrete layers of one or more of these materials can be laid down in a coating by operating the corresponding sputtering cathode(s) selectively. Thus, for example, a titanium implant having a coating can be made by sputtering substantially only HA onto a titanium surface of the implant, then sputtering a mixture of Ag and HA to form a mixed Ag-HA layer, then sputtering a mixture of Ag, HA, and DLC to form a mixed Ag-HA-DLC layer, then sputtering a mixture of Ag and DLC to form a mixed Ag-DLC layer, and finally sputtering substantially only DLC to form an outer DLC layer. In such an example, HA (or borosilicate glass used in its place) can serve to anchor the coating to the titanium surface, Ag mixed with the HA and DLC materials can release Ag ions and exert an antimicrobial effect, and DLC can inhibit adhesion of bacteria and other biomaterials to the coated implant.

The bactericidal active component of the coatings described herein is Ag (or, optionally, another of the antimicrobially effective metals described herein). Pure silver films tend to exhibit greater bactericidal activity than mixed composition films. Mixed composition films that can be used include those which include one or more of DLC, borosilicate, sapphire, and quartz—in addition to Ag.

Other known methods of depositing materials (i.e., other than sputter deposition) on an atom-by-atom or molecule-by-molecule basis can be used to form the coatings described here. By way of example, physical or chemical vapor deposition techniques (e.g., electron beam vapor deposition) can be used. Where substantially uniform coating of implant surfaces is desirable, the implant, the deposition source, or both, should be moved relative to one another during deposition of the coating. A variety of methods of achieving such relative movement are known, including use of turntables, for example.

Thin-films, on the order of 10 nm to 10 micrometers thick, can be readily synthesized using sputtering techniques. Sputtered films have several major advantages when compared to films grown using other technologies. Those advantages include excellent adhesion to many substrate materials, outstanding compositional control when deposited from multiple sources, ability to form discrete layers or allow atomic mixing, and the technique is applicable as a deposition method for most materials. Other deposition techniques, such as thermal or e-beam evaporation (i.e., electron beam vapor deposition) can also be used to create the films.

Sputtering of Ag is simple with a direct current (DC) power supply connected to a DC magnetron cathode. For films containing silver only, a two-inch cathode can be used and linear deposition rates are found for powers between 10 and 200 Watts. Generally, for coatings described herein, the Ag-target power was not limited by technical issues but was limited by the slow rate of deposition of the companion materials in the composite films. For example, when silver was mixed with glass or carbon, it was considered desirable to maintain the Ag content at or below 50% and to couple the Ag deposition rate with the relatively slower deposition rates of glasses and carbon by limiting power to the Ag source.

Diamond-like carbon can be grown with an RF table power at 20 W, a three-inch cylindrical RF magnetron cathode at between 20 W and 120 W, and a mixture of H and Ar gases with the H between 10-15% of the total gas flow rate, for example. Oxide glasses (e.g., borosilicate glasses) can be sputtered with the oxygen recombining at the film surface with the other materials using RF magnetron sputtering. Layers can be made either by turning power supplies on and off as required or by using system shutters.

For coatings that require heat treatment, one method that can achieve the heating is by using a meander molybdenum resistive heater capable of reaching temperatures in excess of 1000° C. The temperature can be controlled using a PID controller and a thermocouple temperature sensor.

Others demonstrated the bactericidal properties of nano-particulate Ag in the 10-25 nanometer particle size range (Melaiye et al., 2005, J. Am. Chem. Soc. 127:2285; Samuel et al., 2004, Int. J. Antimicrob. Agents 23S1:S75). Others focused on nano-scale silver embedded in polymers that could be sprayed onto implant surfaces (Lee et al., 2010, Colloids and Surfaces A/Physicochem. Eng. Aspects 355: 167; Boccaccini et al., 2010, Composites Sci. Technol. 70:1764). In those investigations, the materials are shown to have bactericidal properties.

Mixtures of Ag and HA exhibit antibacterial properties but the bone growth characteristics have not been fully investigated (Chen et al., 2006, Biomaterials 27:5512). Nano-particulate Ag in cement is shown to have bactericidal properties (Alt et al., 2004, Biomaterials 25:4383). There seems to be very little evidence that the particle size of the Ag is important but most of the work employs nano-particulate Ag.

Silver's bactericidal properties have been investigated when mixed with hydroxyapatite, bioactive glasses, carbon, and polymers in bulk form (Boccaccini et al., 2010, Composites Sci. Technol. 70:1764; Verne et al., 2005. Biomaterials 26:5111; Zhao et al., 2006, Nucl. Instrument. Meth. Phys. Res. B 243:299; Travan et al., 2010, "Silver-Polysaccharide nanocomposite antimicrobial coatings for methacrylic thermosets", Acta Biomaterialia). Bacteria should not become resistant to the permeation of ions through cell walls providing damage to the wall as noted in some recent transmission electron microscopy work (Jung et al., 2008, Appl. Environ. Microbiol. 74:2171; Shrivastava et al., 2007, "Characterization of enhanced antibacterial effects of novel silver nanoparticles", Nanotechnology 18). In the TEM micrographs, it was clear that the walls of the bacteria treated with Ag-ions were damaged allowing the cell contents to be released. The core of the treated bacterium became more electron-transparent. Investigators also reported evidence of cell wall separation and electron-dense residues outside the damaged walls of Ag-treated bacteria (Travan et al., 2010, "Silver-Polyaccharide nanocomposite antimicrobial coatings for methacrylic thermosets", Acta Biomaterialia). Colloidal silver films deposited by various methods on titanium have been shown limited antibacterial effects for coated pins implanted into sheep (Meyer et al., 2004, Osteo. Trauma Care 12:81).

Results obtained using continuous sputtered Ag films described herein demonstrate effective bactericidal properties as well. Since the parameters of sputtered film growth provides a method for varying grain-size, investigations of the antibacterial properties of films with varying grain size provide a systematic approach to measuring the particle dependence of the bactericidal property of Ag.

Diamond-Like-Carbon: A Bio-Inert Material

Diamond-like-carbon (DLC) materials have been investigated for several years now for applications exploiting their reduced surface friction and enhanced elastic moduli (Wang et al., 2006, Carbon 44:1826; Loir et al., 2005, Appl. Surface Sci. 247:225). The fact that they can be deposited at room temperature on many types of substrates and have excellent adhesion properties helps to make these materials low-cost candidates for protective coating applications. Recently there has been significant work investigating DLC materials and their biocompatibility with significant successes (Liu et al., 2008. Colloids and Surfaces B: Biointerfaces 61:182; Jones et al., 2010, Diamond & Rel. Mater. 19:685; Hauert et al., 2003, Diamond & Rel. Mater. 12:583; Grill, 2003. Diamond & Rel. Mater. 12:166; Dearnaley et al., 2005, Surface & Coatings Technol. 200:2518).

Two-component systems are the simplest of a large group of multi-component materials. Developing knowledge regarding the compatibility of the constituent materials of these multi-component coatings requires extensive research investigating these relationships. DLC films have been synthesized in the presence of metal ions (Paul et al., 2009, Appl. Surface Sci. 255:8076; Sonoda et al., 2009, Vacuum 84:666). Co-deposition of DLC with tantalum and titanium has demonstrated that DLC is compatible with metals and can retain many of the mechanical properties that make DLC an attractive coating material (Wang et al., 2011, Appl. Surface Sci. 257:1876; Ouyang et al., 2009, Wear 266:96; Harris et al., 1996, Tribology Lett. 2:375). However, most important is the fact that the presence of DLC seems to suppress the formation of biofilms—the films that isolate foreign objects in the human body and tend to encapsulate implants (Liu et al., 2008, Colloids and Surfaces B: Biointerfaces 61:182; Raulio et al., 2008, J. Ind. Microbiol. Biotechnol. 35:751; Laube et al., 2007, J. Urol. 177:1923). Bacteria trapped in biofilms can be responsible for infections near the surface of the implant and would render antibacterial coatings less effective (Habash et al., 1999, J. Clin. Pharmacol 39:887).

Investigating the compatibility of Ag and DLC is an important step in employing these dual functional coatings in biological systems (Choi et al., 2008, Diamond & Rel. Mater. 17:252; Qiua et al., 2005, J. Crystal Growth 284: 470). Some work was performed by others which investigated properties of DLC-Ag composite films. However, those investigations did not involve atomic mixing as the deposition of the two materials was either performed sequentially (i.e., in layers) with poorly adhering Ag on the surface of a DLC or by two different methods where one was not an atom-by-atom deposition process (Habash et al., 1999, J. Clin. Pharmacol 39:887; Choi et al., 2008, Diamond & Rel. Mater. 17:252).

Ag ions can permeate DLC coating from Ag clusters or from a continuous layer of Ag below the surface of a DLC coating. Because Ag inherently has difficulty binding to the surface of DLC, the properties of DLC as a permeation barrier are important. Mixing DLC and Ag can improve the hardness and adhesion of the mixture to implants. Such mixing can also impart mechanical properties of DLC to Ag-containing coatings. As described herein, we achieved good adhesion DLC- and Ag-containing films to anodized titanium (the material used in intramedullary rods).

Silver Salts as Coatings

Ag exhibits bactericidal properties both upon bacterial cells that are in direct contact with an Ag-containing surface and upon bacterial cells that do not directly contact the Ag-containing surface. Without being bound by any particular theory of operation, it is believed that the non-contact bactericidal effect of Ag is mediated by Ag ions. Thus, it is important to consider the solubility of Ag ions in a biological fluid that contacts an implant surface. If a coating that surrounds an Ag-containing material is impervious to both the biological fluid and to Ag ions, then the bactericidal effect of Ag can be expected to be exerted only at physical locations where the coating is cracked, scratched, or worn away. The fragility of DLC coatings on flexible surfaces is known. It is believed that a DLC coating that surrounds an Ag-containing material permits contact between a body fluid outside the coating and the Ag-containing material at discontinuities in the DLC coating, such as at 'cracks' in the coating. Similarly for mixed Ag- and DLC-containing coatings, contact between body fluid and Ag can be expected at Ag-containing regions of the coating, including those on the exterior surface of the coating and those exposed through cracking, wear, or fracture of the coating.

Applying these coatings at room temperature allows them to be used on almost any stable substrate. It also can significantly reduce the cost and complexity of manufacturing. If the goal is long-term, spatially localized bactericidal applications, pure silver (Ag), silver/aluminum oxide (Ag/AlO), or silver/diamond-like carbon (Ag/DLC) films can be utilized. Silver has a low dissolution rate and therefore bactericidal properties will be localized at or very near the silver-coated surface. For these applications, excellent adhesion is required because scratches become unprotected areas that can allow bacteria to grow. The success described herein with room temperature deposition of strongly adhered films minimizes scratching of the films during handling.

To achieve long-range bactericidal action, Ag-containing films must be designed that have a high enough dissolution rate so that silver ions are present in a high concentration at a distance from the substrate. Silver oxide films (AgO and $Ag_2O$) have a higher dissolution rate than pure Ag. Furthermore, silver nitrate ($AgNO_3$), which can be produced using nitrogen during the deposition of AgO or $Ag_2O$ will produce an even higher dissolution rate.

The observations of these different dissolution rates is directly related to Ag—O bond strength. AgO has a cubic crystal structure, while $Ag_2O$ can form a cubic or hexagonal crystal structure depending on oxygen partial pressure and deposition rate-controllable parameters in the deposition methods described herein. The Ag—O bond strengths in order from strongest (shortest bond length) to weakest (longest bond length) are cubic $Ag_2O$ (0.206 nm), AgO (0.208 nm), and hexagonal $Ag_2O$ (0.216 nm). The bond length/strength appears to be important since the weaker the Ag—O bonds, the higher the dissolution rates and the faster the bactericidal action.

By mixing reactive gases (e.g., oxygen containing gases such as $O_2$ and nitrogen containing gases such as $N_2$) during deposition, the dissolution rate can be further modified. Nitrogen atom substitutions on the oxygen-sites occur as determined from the distortion of the x-ray diffraction peak positions which measures atomic plane spacing in solids. Therefore, addition of nitrogen during room-temperature reactive sputtering results in $AgO_{1-x}N_x$ and $Ag_2O_{1-x}N_x$. According to Fourier transform infrared spectroscopy measurements, nitrogen addition further weakens the bond strength and therefore results in an increased silver dissociation rate.

This understanding provides a technique for selecting the dissolution rate and the rate of bactericidal action of the coatings. Multilayered coatings can be engineered to provide both long-term localized bactericidal action and short-term long-range bactericidal action.

As noted above, we can control the rate of dissolution by varying the composition and crystal structure of the films. In addition, this can be changed during the deposition process to create a multilayer film. For example, we can engineer a film that quickly releases a high concentration of silver ions to immediately kill bacteria that may have been introduced during surgery. After this quick release, the film could have a region that releases silver ions at a relatively steady rate for 3-4 weeks to kill bacteria during the early stages of the healing process. Finally, the film could reach a point where there is long term, localized bactericidal protection on the implant. The precise design of such a multilayer film (and its dissolution properties) can be determined from the information presented herein and confirmed through ordinary experimentation by practitioners in this field. Ag-containing films, in which oxygen is a major component, provide desirable long-range bactericidal action (i.e., can exhibit bactericidal activity against bacteria which do not contact the film.

To date, we have deposited silver-containing films by elemental magnetron sputtering or by reactive magnetron sputtering. Ag films are deposited by either direct current (DC) or radio frequency (RF) sputtering. Higher deposition rates are achieved using DC sputtering but both are effective. AgO, $Ag_2O$, $AgO_{1-x}N_x$ and $Ag_2O_{1-x}N_x$ are synthesized by sputtering in a reactive gas mixture of argon (Ar or any other non-reactive gas), O and N.

Depending on the geometry of the substrate, cathodes can be designed to generate uniform coatings over the surface. For example, a rod can be coated using a cathode with cylindrical symmetry directing the material inward incident on the outside substrate surface. Alternatively, the substrate may be rotated. In addition, a cathode can be designed that sputters outward to coat the inside of a cylindrical tube.

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

Example 1

Here we describe results that establish the tractability of our proposed product. We present preliminary results on 1) adjusting the size of the crystallites in the silver films on stainless steel and titanium substrates, 2) the bactericidal effects of silver films against *S. aureus,* 3) the adhesion of silver deposited under various conditions to stainless steel and titanium substrate materials, and 4) some of our experience in synthesis of DLC materials.

Bactericidal Property of Silver Thin-Films

Crystallite Size of Silver Films Dependence on Deposition Conditions

Much work has been performed that assumes that nanoparticulate silver is required to be effective as an antibacterial material (e.g., Sheikh et al., 2009, Physica E 42:132 and Shahverdi et al., 2007, Nanomed. Nanotechnol. Biol. Med. 3:168). Little work has been reported that addresses any size dependence of the silver particles.

The first step in performing the required systematic study is creating particles of different sizes or films with varying grain sizes. In this section we present experimental results that demonstrate our ability to modify the grain size and microstructure of Ag films on titanium and stainless steel substrates. Silver films on titanium and stainless steel substrates were grown using a sputter deposition technique. FIG. 1 shows two scanning electron micrographs (SEMs) of Ag films grown under different deposition conditions.

Figure 2B:
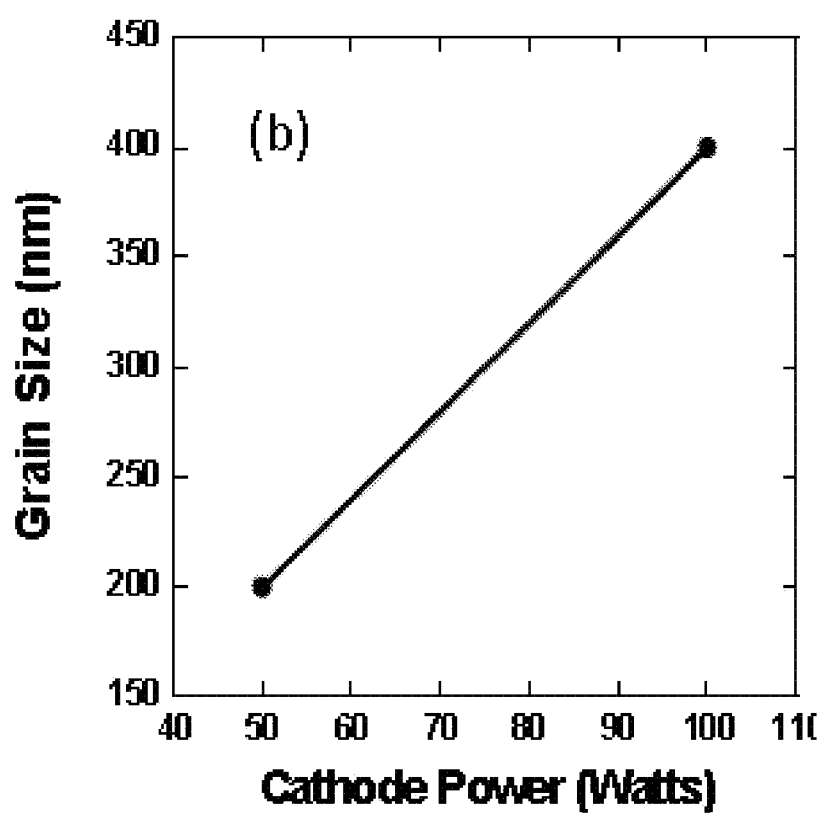
In FIG. 2B, grain size is reported as a function of the cathode power used during deposition.
Figure 2C:
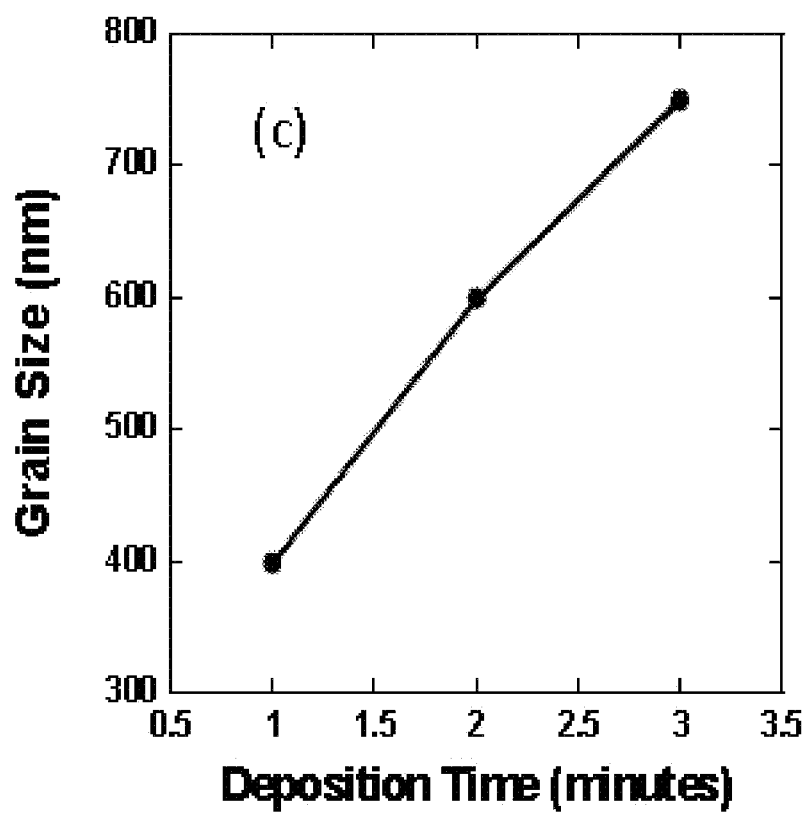
In FIG. 2C, grain size is reported as a function of the deposition time (i.e., layer thickness) used during deposition. Parameters not indicated on the abscissa were held constant during the depositions corresponding to the data points shown.

Investigations of Ag depositions onto polished titanium and stainless steel substrates confirm these expectations. The microstructure as measured using SEM micrographs of representative films are shown in FIG. 1 demonstrating the variation in microstructure resulting from different deposition conditions. As part of the evaluation of the temperature and power dependence of adhesion (film thickness was not important), we were able to create samples where only temperature or power was modified so that direct comparisons of grain size could be made. FIG. 2 represents a summary of these results where the average of the size of several grains has been used.

Anti-Bacterial Property of Silver Films

Gram-positive bacteria ATCC27660 *Staphylococcus aureus* (*S. aureus*) was used to investigate the anti-bacterial property of the sputtered Ag films. Single colonies of *S. aureus* were grown by streak nutrition agar plates with frozen stock and incubated overnight at 37° C. and isolated colonies were obtained. A single colony was transferred to Luria-Bertani (LB) growth medium in a test tube and incubated for 24 hours at 37° C. with vigorous shaking.

Sterilized Ag-coated and uncoated sections of titanium intramedullary implants were placed in the bacteria solutions and incubated for 24 hours. The implant sections were then removed and incubated overnight at 37° C. Scrapings from the Ag coated section of the implant, an uncoated section of the implant, and a section of an Ag coated stainless steel implant were incubated in LB for 24 hours and compared to controls that contained only LB and *S. aureus*. After the incubation period, the scattering of 600 nm light was measured using a Perkin Elmer Lambda UV-Vis absorbance spectrophotometer as an indicator of bacterial growth.

The scattering at 600 nm light is directly proportional to cell density, with the exact numeric relationship being species dependent generally in the ranges $10^8$-$10^9$ colony forming units per 1.0 absorbance unit. It is worth outlining the expected outcomes of this measurement since the spectrophotometer is generally used to measure absorption. Scattering and absorption result in the same behavior as recorded by the spectrophotometer—a numerical value related to the scattering of >1 suggests that the bacteria density is near maximum and unable to rapidly divide (i.e., the bacteria are likely in the stationary phase). Scattering numbers of 0.1-0.9 indicate cell density where the bacteria will most rapidly divide (i.e., the bacteria are likely in the logarithmic growth phase).

The scattering results for light of wavelength 600 nm through bacteria suspensions grown from different scrapings are summarized in Table 1. Any bacteria, dead or alive, will scatter the light so this is a count of all bacteria contained in the solution. If the bacteria were dead when the scraping was made, the bacteria would not reproduce and scattering will be relatively minimal. Broth from the scrapings of the Ag-coated materials measure the smallest light scattering values indicating the smallest density of bacteria. Titanium metal has no discernible bactericidal effect while it is found that when an Ag film is present, the substrate the Ag is deposited onto does not appear to affect the bactericidal property of Ag.

TABLE 1

Results of bacteria light scattering experiments. The light used had a wavelength of 600 nm.

| S. aureus | Titanium (uncoated backside) | Ag-Coated Titanium | Ag-Coated Stainless Steel |
|---|---|---|---|
| | Quantitative Scattering of 600 nanometer light | | |
| Trial 1 | 2.5 | 2.5 | 0.022 | 0.026 |
| Trial 2 | 2.5 | 2.5 | 0.044 | |
| Trial 3 | 2.5 | 2.5 | 0.032 | |
| Trial 4 | 2.5 | 2.5 | 0.041 | |

While the quantitative light scattering measurements are very important to the presentation of the results, perhaps the most convincing evidence for the bactericidal properties of silver films was visually observed. The two nutrient solutions obtained from the silver coated region of the titanium intramedullary implant were visually clear. By contrast, nutrient solutions obtained from the non-coated region of the titanium intramedullary implant were plainly cloudy, indicating substantial bacterial survival (and subsequent growth in the medium). The cloudiness observed in the test tube containing the non-coated scraping was dramatic evidence of the reproduction of the living bacteria.

Adhesion of Silver Films to Titanium Substrates

Adhesion of Ag on polished titanium substrates was investigated. The materials science community defines standard procedures for adhesion tests. We used the ASTM D3359 test which employs 3M 610 cellophane tape. The tape is applied to the film and then peeled back at any angle the user selects. This action will peel the film coating with the tape for a poorly adhered film while having little or no impact on a strongly adhered film. This test will measured the strength of the tape-glass bond in comparison to the glass-plastic substrate bond. It should be noted that this is a very demanding test for the material/substrate interface, i.e. even if the film adheres to the tape better than the substrate, the film may still be considered as well adhered to the substrate.

Our measurements were made removing the cellophane tape while pulling on the tape parallel to the tape-implant interface. On the polished substrates the silver film/titanium substrate adhesion was strong only when the films were deposited at temperatures of 300° C. or greater. At 275° C. the films consistently adhered better to the cellophane tape than to the substrate. On sections of intramedullary implant with an anodized titanium surface, preliminary results suggest that the film/substrate adhesion is significantly better than the polished substrates but for temperatures below 275° C. patches of silver lifted from the substrate in the adhesion test.

Depositions of Ag co-deposited with either borosilicate glass or alumina, at room temperature, results in strongly adhering films. Preliminary measurements of the bactericidal properties indicated that the coatings were still effective.

Example 2

Diamond-Like Carbon and Borosilicate

We sputtered DLC onto silver substrates and found excellent adhesion. We sputtered borosilicate onto many substrates including metals and found excellent adhesion. These materials are biocompatible and have permeation barrier properties. We used these materials as seed layers and as a mixture with Ag to improve low temperature adhesion. Both materials are expected to be useful as Ag permeation control layers to limit the amount of Ag that goes into ion form in blood plasma.

Our research resulted in verifying the following critical attributes and capabilities of our film products:

Proven capability for depositing Ag on polymer (i.e. "plastic") substrates.

Proven capability to coat medical grade metals (stainless steel and titanium) with a broad-spectrum bactericidal coating (Ag) at room temperature with excellent adhesion.

Developed methods for effectively "hiding" the Ag coating from the body by depositing diamond-like carbon (DLC). This prevents the formation of a biofilm which could hinder the performance of the Ag bactericidal coating.

Proven capability to tailor the concentration profile of Ag on the medical device thereby controlling the release of Ag+ as a function of time.

Proven capability for increasing the hardness of the Ag coating thereby reducing the potential for scratches to the coating to occur during surgery that could allow infection.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. An article that is implantable in an animal, the article comprising a microparticulate silver-containing antimicrobial layer stably adhered upon at least one surface of the article, the layer having a proximal zone and a distal zone, wherein the distal zone comprises silver oxide microparticles, wherein the rates of release of silver ions from the proximal zone and distal zone are different upon implanting the article in the animal, wherein the antimicrobial layer is formed on and stably adhered to the surface of the article by sputtering silver oxide microparticles onto the surface;
   wherein said antimicrobial layer is a continuous layer of 10 nm to 10,000 nm thickness and is applied at room temperature, and wherein the rates of release are controlled by the bond strength of the silver oxide microparticle crystal structure and wherein the silver oxide microparticle crystal structure is dependent upon the oxygen partial pressure and deposition rate of the sputtering process.

2. The article of claim 1, wherein the antimicrobial layer is stably adhered upon substantially the entire surface of the article.

3. The article of claim 1, wherein the antimicrobial layer further comprises silver, nitrogen-containing silver oxides, or both.

4. The article of claim 1, wherein the antimicrobial layer comprises diamond-like carbon (DLC).

5. The article of claim 4, wherein the antimicrobial layer comprises a substantially uniform mixture of DLC and microparticles comprising a silver oxide.

6. The article of claim 4, wherein the antimicrobial layer comprises a proximal zone having a higher ratio of silver-oxide-containing microparticles to DLC than a distal zone.

7. The article of claim 1, wherein the antimicrobial layer is laminated between the surface of the article and an exterior layer comprising DLC.

8. The article of claim 7, wherein the exterior layer consists essentially of DLC and has a porosity sufficient to permit an antimicrobially effective amount of silver ion to leach from the antimicrobial layer to the distal surface of the exterior layer when the article is implanted in an animal.

9. The article of claim 1, wherein the article is selected from the group consisting of intramedullary nails, pins, rods, plates, screws, artificial joints, artificial heart valves, artificial heart components other than valves, prosthetic blood vessels, catheters, stents, pacemaker components, nerve-interface electrodes, wound dressings, surgical stitching fibers, and pharmaceutical depots.

10. The article of claim 1, wherein the difference in the rate of release of silver ion from the proximal zone and distal zone is attributable to a difference between the relative amounts of silver oxides in each of the proximal zone and distal zone.

11. The article of claim 1, wherein the difference in the rate of release of silver ion from the proximal zone and distal zone is attributable to differences between relative amounts of silver oxides and another material in each of the proximal zone and distal zone.

12. The article of claim 11, wherein the other material is selected from the group consisting of diamond-like carbon (DLC), borosilicate, sapphire, quartz, and hydroxyapatite.

13. The article of claim 1, wherein at least one of the proximal zone and distal zone includes microparticles comprising a silver oxide.

14. The article of claim 1, wherein the microparticles have an average size in the range of 10 to 2000 nm.

15. The article of claim 1, wherein the microparticles have an average size in the range of 10 to 100 nm.

16. The article of claim 1, wherein the antimicrobial layer is formed by co-deposition of (1) silver oxide with (2) carbon or a glass or alumina.

17. The article of claim 16, wherein said carbon is diamond-like carbon (DLC).

18. The article of claim 1, wherein said proximal zone further comprises silver metal microparticles.

19. The article of claim 1, wherein said sputtering is reactive sputtering and comprises a reactive gas selected from the group consisting of oxygen, and nitrogen/oxygen mixtures.

* * * * *